United States Patent
Oh et al.

(10) Patent No.: US 8,273,128 B2
(45) Date of Patent: Sep. 25, 2012

(54) SLIDING INTERVERTEBRAL IMPLANT METHOD

(75) Inventors: YoungHoon Oh, Montville, NJ (US); Mahmoud F. Abdelgany, Rockaway, NJ (US)

(73) Assignee: Custom Spine, Inc., Parsippany, NJ (US)

( * ) Notice: Subject to any disclaimer, the term of this patent is extended or adjusted under 35 U.S.C. 154(b) by 230 days.

(21) Appl. No.: 12/938,922

(22) Filed: Nov. 3, 2010

(65) Prior Publication Data

US 2011/0046738 A1 Feb. 24, 2011

Related U.S. Application Data

(62) Division of application No. 11/869,798, filed on Oct. 10, 2007, now Pat. No. 7,850,734.

(51) Int. Cl.
*A61F 2/44* (2006.01)
(52) U.S. Cl. ..................................... 623/17.16
(58) Field of Classification Search ..... 623/17.11–17.16
See application file for complete search history.

(56) References Cited

U.S. PATENT DOCUMENTS

| | | | |
|---|---|---|---|
| 5,290,312 A * | 3/1994 | Kojimoto et al. | 623/17.15 |
| 6,773,460 B2 | 8/2004 | Jackson | |
| 6,830,589 B2 | 12/2004 | Erickson | |
| 6,863,673 B2 | 3/2005 | Gerbec et al. | |
| 6,893,464 B2 | 5/2005 | Kiester | |
| 7,018,415 B1 | 3/2006 | McKay | |
| 7,083,650 B2 | 8/2006 | Moskowitz et al. | |
| 7,094,257 B2 | 8/2006 | Mujwid et al. | |
| 7,217,293 B2 | 5/2007 | Branch, Jr. | |

* cited by examiner

*Primary Examiner* — Sameh Boles
(74) *Attorney, Agent, or Firm* — Rahman LLC

(57) ABSTRACT

A method includes a first member that connects to an intervertebral space between two adjacent vertebrae. The first member includes a pair of curved side walls connected to each of a front wall, an upper curved wall, and a lower curved wall, wherein a length of a first curved side wall is less than a length of each of a second curved side wall, the upper curved wall, and the lower curved wall, and wherein an edge of the second curved side wall is offset from an edge of the front wall. A second member is slidably attached to the first member, and includes a top and bottom curved wall each connected to an inclined side wall and a guide wall, wherein the guide wall includes grooves, wherein the second curved side wall of the first member slides in the grooves of the guide wall.

18 Claims, 5 Drawing Sheets

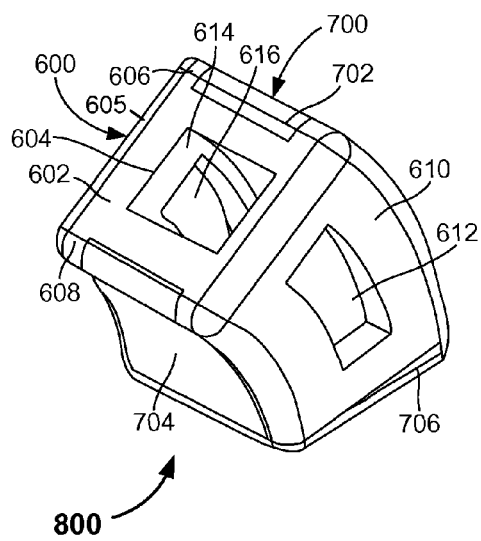
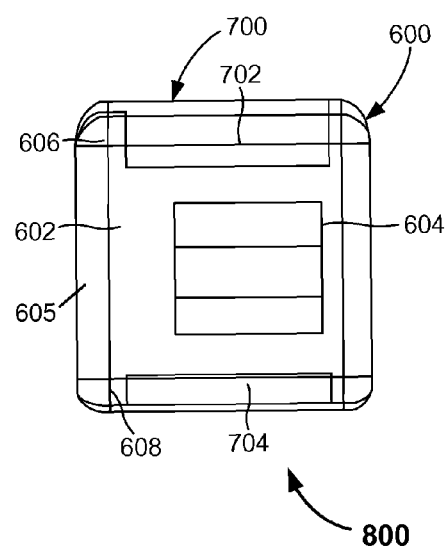
FIG. 3A    FIG. 3B
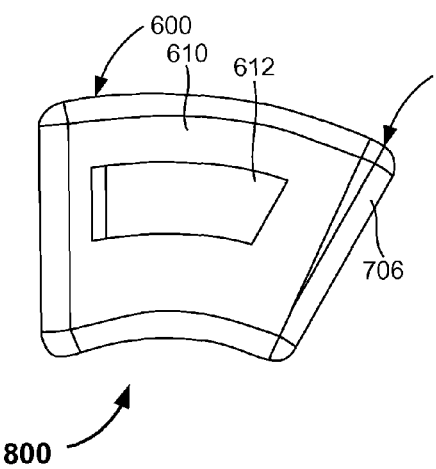
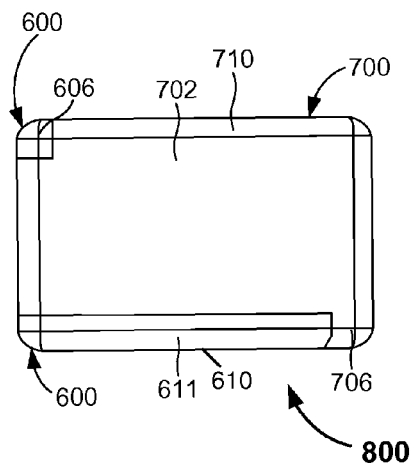
FIG. 3C    FIG. 3D

FIG. 4A  FIG. 4B

SLIDING INTERVERTEBRAL IMPLANT METHOD

CROSS REFERENCE TO RELATED APPLICATION

This application is a divisional of U.S. patent application Ser. No. 11/869,798 filed on Oct. 10, 2007, now U.S. Pat. No. 7,850,734, the contents of which, in its entirety, is herein incorporated by reference.

BACKGROUND

1. Technical Field

The embodiments herein generally relate to medical devices, and, more particularly, to a sliding intervertebral implant used during orthopedic surgeries.

2. Description of the Related Art

Spinal fusion procedures may comprise the entire removal of the degenerated intervertebral disc between two adjacent vertebrae and the insertion of an implant within the intervertebral space. The implant may be positioned to maintain the spine alignment and the height and angle of the intervertebral space by pushing the vertebrae apart from each other, which helps in providing stability and proper maneuvering of the spine. Lastly, fusion material may be placed within the intervertebral space, which along with the body's natural cells, promotes bone formation. The fusion occurs between the endplates of the vertebrae.

A variety of implants of different configurations for intervertebral space have been developed to accomplish the spinal fusion surgeries. Some examples include spinal fusion cages, threaded bone dowels, stepped bone dowels, etc. The spinal fusion cages are mostly used as they are easy to handle. However, these cages offer some limitations. The spinal fusion cages generally do not maintain the spine alignment and the angle and height of the intervertebral space, thus the natural curvature of the spine may be changed. Also, it is typically very difficult to insert a spinal fusion cage into the vertebrae as they contain intricately combined parts. The wedge implants also suffer from certain drawbacks such as limited ability to prevent rotational forces between the vertebrae.

Most of these traditional intervertebral space implants are designed for either one-piece or multiple-pieces. For one-piece design, the implants are generally not accommodated to extend their surface contact in situ. Thus, to increase stability between two adjacent vertebrae, they generally have to be increased in size or inserted as a pair. For multiple assembly design, on the other hand, those parts are separated with rotational joints or expanded in heights (towards adjacent vertebral bodies). Generally, these tend to lack translation for all directions or have a limitation of rotation to increase the moment arm. Also, these devices are typically unable to sustain forces from the adjacent vertebrae and provide sufficient stability to the spine. Accordingly, there remains a need for a new intervertebral implant to restore motion in a patient's back in a controlled manner while permitting natural motion with stability.

SUMMARY

In view of the foregoing, an embodiment herein provides a method of performing a surgical procedure, the method comprising engaging an intervertebral sliding implant in a non-extended position to a vertebral body. The intervertebral sliding implant comprises a first member adapted to connect to an intervertebral space between two adjacent vertebrae, wherein the first member has a curved configuration and comprises a pair of curved side walls connected to each of a front wall, an upper curved wall, and a lower curved wall, wherein a length of a first curved side wall is less than a length of each of a second curved side wall, the upper curved wall, and the lower curved wall, and wherein an edge of the second curved side wall is offset from an edge of the front wall. The intervertebral sliding implant comprises a second member slidably attached to the first member, wherein the second member has a curved configuration and comprises a top and bottom curved wall each connected to a truncated inclined side wall and a guide wall positioned opposite to the truncated inclined side wall, wherein the guide wall comprises a plurality of oppositely positioned grooves. The method includes adjusting the inner member according to the intervertebral space of the vertebral body; aligning the second curved side wall of the first member in the plurality of grooves of the second member; and sliding the second curved side wall of the first member in the plurality of grooves of the second member within a limitation of a pre-set curvature to an extended position, wherein the pre-set curvature is based on a pattern of an outer shape of the intervertebral space.

The front wall may comprise a leg positioned along an edge of the front wall adjacent to the second curved side wall, and wherein a height of the leg of the front wall is substantially equal to a height of the first curved side wall. The height of each of the leg of the front wall and the first curved side wall may be greater than a height of each of the front wall and the second curved side wall. The first member and the second member may be adapted to articulate from an extended position to a non-extended position as the first member slides into the second member, and wherein the first curved side wall of the first member may be adapted to connect to the truncated inclined side wall of the second member in the non-extended position. Each of the front wall, the first curved side wall, and the second curved side wall of the first member may comprise a gap, wherein the method may further comprise inserting bone fusion material in the sliding intervertebral implant through each the gap in the non-extended position.

Another embodiment provides a method comprising positioning a first member into an intervertebral space between two adjacent vertebrae, wherein the first member comprises a substantially curved configuration and a pair of curved side walls operatively connected to each of a front wall, an upper curved wall, and a lower curved wall, wherein a length of a first curved side wall is less than a length of each of a second curved side wall, the upper curved wall, and the lower curved wall, wherein an edge of the second curved side wall is offset from an edge of the front wall, and wherein the front wall comprises a leg positioned along an edge of the front wall adjacent to the second curved side wall; positioning a second member to be operatively connected to the first member, wherein the second member comprises a substantially curved configuration and includes a top and bottom curved wall each operatively connected to a truncated inclined side wall and a guide wall, wherein the guide wall is positioned opposite to the truncated inclined side wall, wherein the guide wall comprises a plurality of oppositely positioned grooves, wherein the second curved side wall of the first member is adapted to slide in the plurality of oppositely positioned grooves of the guide wall of the second member within a limitation of a pre-set curvature, and wherein the pre-set curvature is based on a pattern of an outer shape of the intervertebral space; articulating the first member and the second member from an extended position to a non-extended position as the first member slides into the second member; and operatively connecting the first curved side wall of the first member to the truncated inclined side wall of the second member in the non-extended position.

Each of the first curved side wall and the second curved side wall of the first member may comprise a gap. The front wall may comprise a gap positioned offset from a center portion of the front wall. The height of the leg of the front wall may be substantially equal to a height of the first curved side wall. The height of each of the leg of the front wall and the first curved side wall may be greater than a height of each of the front wall and the second curved side wall. The method may further comprise inserting bone fusion material in the gap.

Another embodiment provides a method comprising providing an inner member that is adapted to connect to an intervertebral space between two adjacent vertebrae, wherein the inner member comprises a front wall comprising a leg positioned on a lateral edge of the front wall; a first curved side wall connected to the front wall; a second curved side wall positioned opposite to the first curved side wall and behind the leg; an upper curved wall; and a lower curved wall positioned opposite to the upper curved wall; providing an outer member that is adapted to slidably attach to the inner member, wherein the outer member comprises a top curved wall matching an arcuate shape of the upper curved wall of the inner member; a bottom curved wall matching an arcuate shape of the lower curved wall of the inner member; a truncated inclined side wall connected to each of the top curved wall and the bottom curved wall; and a guide wall positioned opposite to the truncated inclined side wall and comprising a plurality of oppositely positioned grooves, the guide wall being connected to each of the top curved wall and the bottom curved wall; allowing the second curved side wall of the inner member to be adapted to slide in the plurality of oppositely positioned grooves of the guide wall of the outer member within a limitation of a pre-set curvature, wherein the pre-set curvature is based on a pattern of an outer shape of the intervertebral space; allowing the inner member and the outer member to be adapted to articulate from an extended position to a non-extended position as the inner member slides into the outer member; and allowing the first curved side wall of the inner member to be adapted to connect to the truncated inclined side wall of the outer member in the non-extended position.

Each of the first curved side wall and the second curved side wall of the inner member may comprise a gap. The upper curved wall may be greater in length than the first curved side wall. The height of the leg of the front wall may be substantially equal to a height of the first curved side wall. The height of each of the leg of the front wall and the first curved side wall may be greater than a height of each of the front wall and the second curved side wall. The front wall may comprise a gap positioned offset from a center portion of the front wall. The lower curved wall of the inner member may be greater in length than the first curved side wall. The second curved side wall may be greater in length than the first curved side wall. The method may further comprise configuring the gap to permit insertion of bone fusion material in the gap.

These and other aspects of the embodiments herein will be better appreciated and understood when considered in conjunction with the following description and the accompanying drawings. It should be understood, however, that the following descriptions, while indicating preferred embodiments and numerous specific details thereof, are given by way of illustration and not of limitation. Many changes and modifications may be made within the scope of the embodiments herein without departing from the spirit thereof, and the embodiments herein include all such modifications.

BRIEF DESCRIPTION OF THE DRAWINGS

The embodiments herein will be better understood from the following detailed description with reference to the drawings, in which:

FIGS. 3A through 3D illustrate a perspective view, a front view, a side view, and a top view, respectively, of an assembled sliding intervertebral implant including the inner member of FIGS. 1A through 1D and the outer member of FIGS. 2A through 2D in a non-extended position according to an embodiment herein;

FIGS. 4A through 4D illustrate a perspective view, a front view, a side view, and a top view, respectively, of the assembled sliding intervertebral implant of FIGS. 3A through 3D in an extended position according to an embodiment herein.

DETAILED DESCRIPTION OF PREFERRED EMBODIMENTS

Figures 1A, 1B:
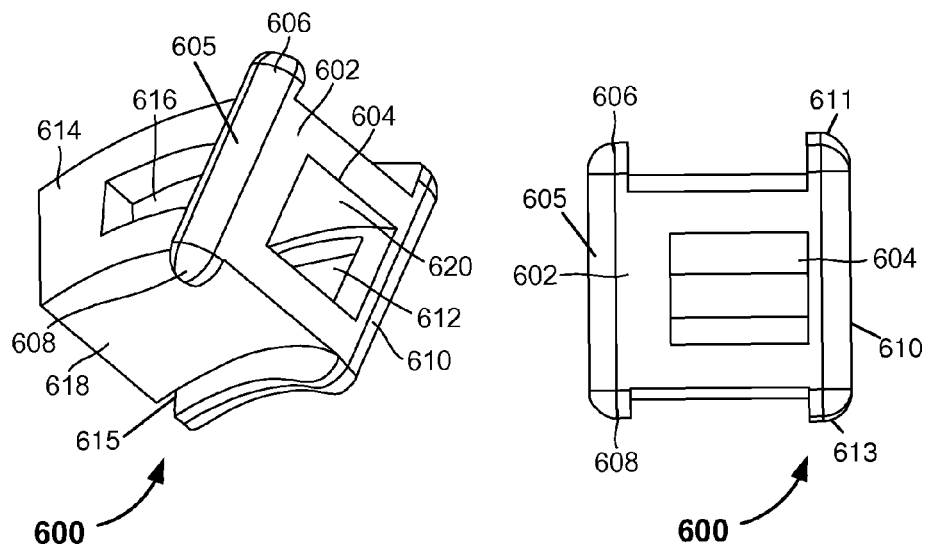
FIGS. 1A through 1D illustrate a perspective view, a front view, a side view, and a top view, respectively, of an inner member of a sliding intervertebral implant according to an embodiment herein.

The embodiments herein and the various features and advantageous details thereof are explained more fully with reference to the non-limiting embodiments that are illustrated in the accompanying drawings and detailed in the following description. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

As previously mentioned, there remains a need for a new intervertebral implant to restore motion in a patient's back in a controlled manner while permitting natural motion with stability. The embodiments herein achieve this by providing a sliding intervertebral implant that attaches to a vertebral body, whereby the sliding intervertebral implant includes an inner member and an outer member that slide with respect to one another within a limitation of a pre-set curvature to an extended position, wherein the pre-set curvature is based on a pattern of an outer shape of the intervertebral space (i.e., space between vertebral bodies). Referring now to the drawings, and more particularly to FIGS. 1A through 5, where similar reference characters denote corresponding features consistently throughout the figures, there are shown preferred embodiments.

FIGS. 1A through 1D illustrate a perspective view, a front view, a side view, and a top view, respectively, of an inner member 600 of a sliding intervertebral implant 800 (as shown in FIGS. 3A through 4D) according to an embodiment herein. The inner member 600 includes a front wall 602 having a first rectangular gap 604, a leg 605 connected to the front wall 602 and having an upper portion 606 and a lower portion 608 positioned opposite to the upper portion 606. The inner member 600 further includes a first curved side wall 610 having a second rectangular gap 612, a second curved side wall 614 positioned opposite to the first curved side wall 610 and having a third rectangular gap 616, a lower curved wall 618, and an upper curved wall 620.

Figures 1C, 1D:
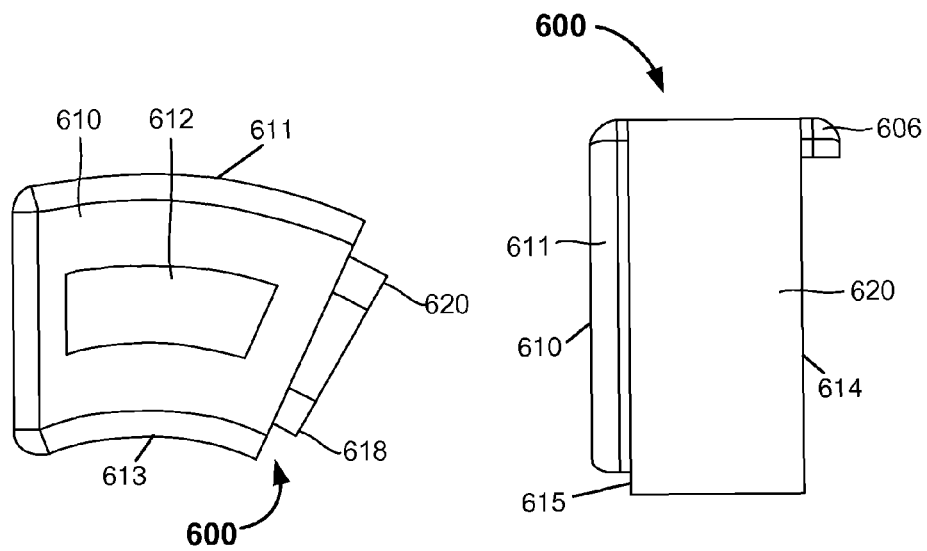

FIG. 1A is a three dimensional perspective view of the inner member 600. The first curved sidewall 610 having the second rectangular gap 612 is coupled to the right side of the front wall 602 having the first rectangular gap 604. The second curved side wall 614 having the third rectangular gap 616 is coupled to the left side of the front wall 602. The upper curved wall 620 is coupled to the upper side of the front wall 602 and the lower curved wall 618 is coupled to the lower side of the front wall 602. The length of the lower curved wall 618 is smaller than that of the upper curved wall 620 thereby creating an overall arcuate shape for the inner member 600. FIG. 1B is the front view of the inner member 600, which illustrates the front wall 602 with the first rectangular gap 604, and the leg 605 with the upper portion 606 and the lower portion 608. Additionally, the upper portion 611 and lower portion 613 of the first curved side wall 610 is also shown having a height substantially equal to the height of the leg 605. FIG. 1C is the side view of the inner member 600, which shows the first curved side wall 610 with the second rectangular gap 612, the lower curved wall 618, and the upper curved wall 620. The length of each of the lower curved wall 618 and the upper curved wall 620 are longer than the first curved side wall 610 thereby creating a notch 615 in the first curved side wall 610. Additionally, the height of the first curved side wall 610 is greater than the height defined by the distance between the lower curved wall 618 and the upper curved wall 620. FIG. 1D is the top view which shows the upper portion 606 of the leg 605, the second curved sidewall 610 with the notch 615, and the upper curved wall 620. The first rectangular gap 604, second rectangular gap 612, and third rectangular gap 616 permit bone and/or other materials (e.g., bone morphogenetic protein (BMP)) to be packed in the implant 800 (of FIGS. 4A through 4D) once implanted in the human body.

Figures 2A, 2B:
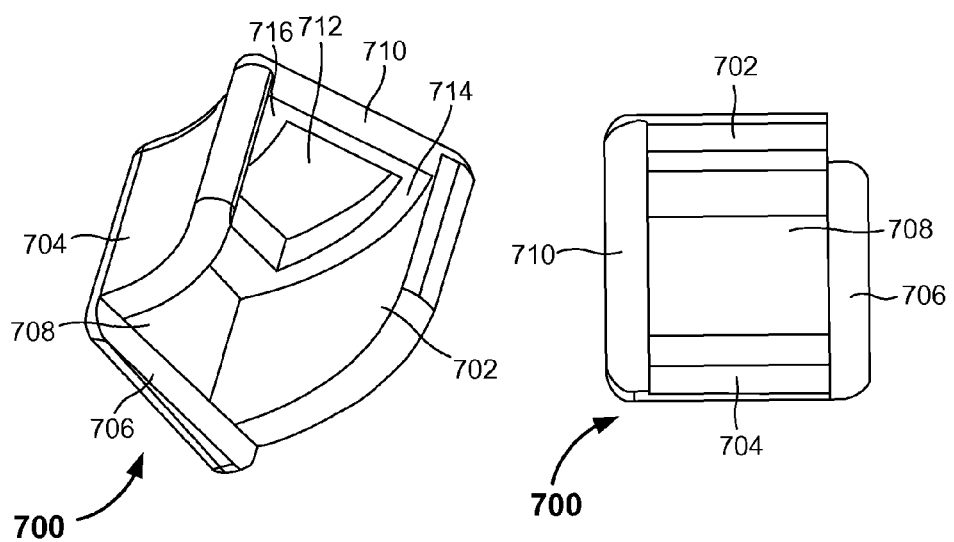
FIGS. 2A through 2D illustrate a perspective view, a front view, a side view, and a top view, respectively, of an outer member of a sliding intervertebral implant according to an embodiment herein

FIGS. 2A through 2D illustrate a perspective view, a front view, a side view, and a top view, respectively, of the outer member 700 according to an embodiment herein. The outer member 700 forms a component of the sliding intervertebral implant 800 (as shown in FIGS. 3A through 4D). The outer member 700 includes a top curved wall 702, a bottom curved wall 704, an inclined side wall 706, a back wall 708, and a guide wall 710 having a rectangular gap 712 and two grooves 714, 716. FIG. 2A is the three dimensional perspective view of the outer member 700. As shown, the outer member 700 generally has an open geometry as the inclined side wall 706 is truncated.

Figures 2C, 2D:
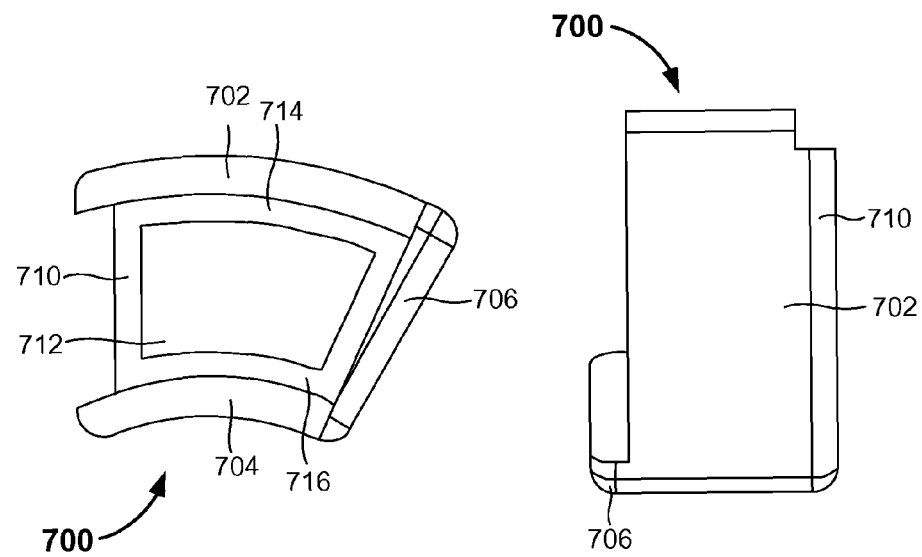

The top curved wall 702 and the bottom curved wall 704 at their bottom side are attached to the back wall 708 whereas the upper sides of the top curved wall 702 and the bottom curved wall 704 are free. Furthermore, both the top curved wall 702 and the bottom curved wall 704 are attached to the inclined side wall 706 at their one side and the other sides are attached to the guide wall 710. FIG. 2B is the front view of the outer member 700, which shows the top curved wall 702, the bottom curved wall 704, the inclined side wall 706, the back wall 708, and the third sidewall 710. FIG. 2C is the side view of the outer member 700, which illustrates the top curved wall 702, the bottom curved wall 704, the inclined side wall 706, and the guide wall 710 having the rectangular gap 712 and the two grooves 714, 716. The length of the top curved wall 702 is longer than the length of the bottom curved wall 704 to create an arcuate shape to the outer member 700. Moreover, the length of each of the top curved wall 702 and the bottom curved wall 704 is larger than the length of the guide wall 710. FIG. 2D is the top view of the outer member 700, which shows the upper side of top curved wall 702, the inclined side wall 706, and the guide wall 710. The rectangular gap 712 permits bone and/or other materials (e.g., bone morphogenetic protein (BMP)) to be packed in the implant 800 (of FIGS. 4A through 4D) once implanted in the human body.

FIGS. 3A through 3D illustrate a perspective view, a front view, a side view, and a top view respectively of a sliding intervertebral implant 800 having the inner member 600 and the outer member 700 in a non-extended position according to an embodiment herein. FIG. 3A is the perspective view of the sliding intervertebral implant 800. The inner member 600 and the outer member 700 are shown interconnected with each other. The top curved wall 702 and the bottom curved wall 704 of the outer member 700 accommodate the inner member 600. The first curved side wall 610 is attached with the inclined side wall 706. The second rectangular gap 612 present on the second side wall 610, the third rectangular gap 616 present on the second curved side wall 614 of the inner member 600, and the rectangular gap 712 present on the guide wall 710 (not shown in FIG. 3A) remain parallel with each other. The upper portion 606 of the leg 605 of the front wall 602 and the upper portion 611 of the first curved side wall 610 of the inner member 600 accommodate the top curved wall 702 of the outer member 700. Similarly, the second leg 608 of the front wall 602, and the bottom portion of the first curved side wall 610 accommodate the bottom curved wall 704. FIG. 3B is the front view of the sliding intervertebral implant 800. The top curved wall 702 and the bottom curved wall 704 are fixed over the upper curved wall 620 and the lower curved wall 618 of FIGS. 1A and 1C.

FIG. 3C is the side view of the sliding intervertebral implant 800. The first curved side wall 610 is connected to the inclined side wall 706. FIG. 3D is the top view. The first leg 606 and the first curved side wall 610 of the inner member 600 are connected to the guide wall 710 and the inclined side wall 706 of the outer member 700. The inner member 600 and the outer member 700 of the sliding intervertebral implant 800 have open geometries for accommodating more surface contact. When the sliding intervertebral implant 800 is inserted into the intervertebral space, the inner member 600 and the outer member 700 remain in the non-extended position; however the members 600, 700 may slide with respect to one another after insertion to sustain forces from the adjacent vertebrae.

There are several options for inserting the assembly 800 into the intervertebral space (not shown). First, the insertion can be performed by placing a long-extendable insertion device (not shown) in the second rectangular gap 612. After the insertion, the insertion device will slide down to position the outer member 700. Another option is that the insertion device holds the front wall 602 in place. After the insertion, the extendable portion of the insertion device pushes the outer member 700 into the desired position.

Figure 4C:
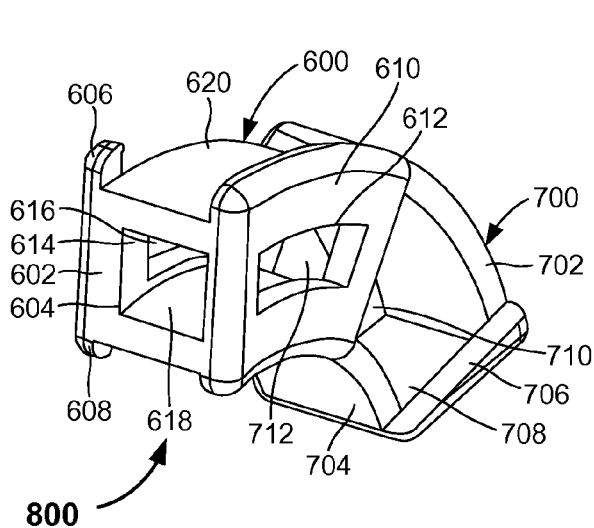
Figure 4C:
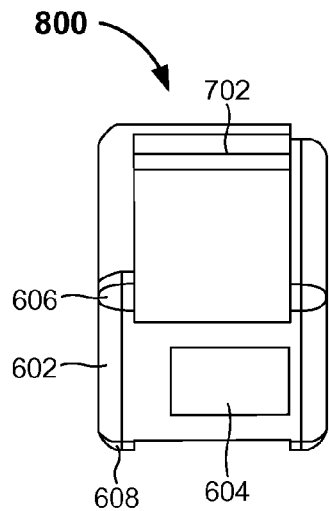
Figure 4C:
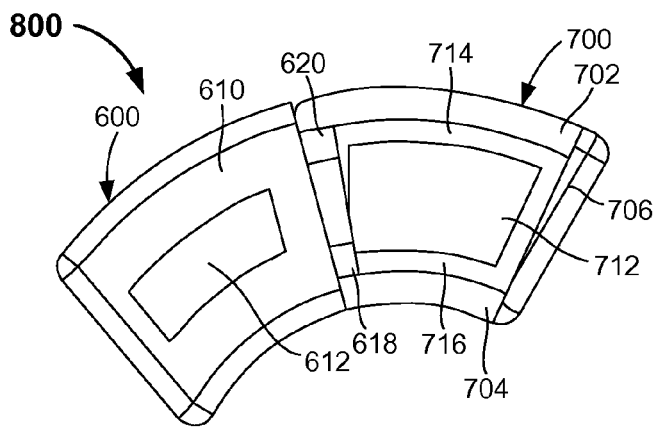

FIGS. 4A through 4D illustrate a perspective view, a front view, a side view, and a top view, respectively, of the sliding intervertebral implant 800 of having the inner member 600 and the outer member 700 in an extendable position according to an embodiment herein. FIG. 4A is the perspective view of the sliding intervertebral implant 800. As shown, both the inner 600 and the outer member 700 are in their fully extended positions. The inner member 600 slides through the outer member 700 in an arcuate path by the help of the first curved side wall 610, which along with the upper curved wall 620 slides into the outer member 700.

Figure 4D:
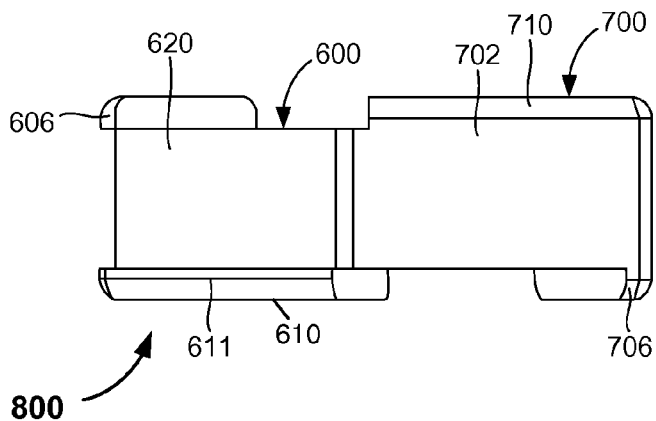

FIG. 4C is the side view of the sliding intervertebral implant 800. As shown, the upper curved wall 620 and the lower curved wall 618 of the inner member 600 slide into the outer member 700 by the help of the grooves 714 and 716. This helps the first curved side wall 610 also to slide. The curved shape of the first curved side wall 610 of the inner member 600 matches with the curved shape of the top curved wall 702 and the bottom curved wall 704 of the outer member 700. FIG. 4D is the top view illustrating the top curved wall 702 of the outer member 700 sliding over the upper curved wall of the inner member 600.

When the sliding intervertebral implant 800 is inserted into the intervertebral space, the final surface contact of the implant 800 does not change (e.g., may remain in the non-extended position of FIGS. 3A through 3D). However, at the final stage, the inner member 600 may fully slide and form an extended position such as an arced structure. This arced structure may increase a length of supporting surface between two adjacent vertebrae by increasing a length of the intervertebral implant 800. After a final extended position of the sliding intervertebral implant 800 is achieved, inserts (e.g. bone, morphogenetic protein (BMP), etc) can be inserted to the gaps 604, 612, 616, 712.

After the inner member 600 is inserted into the outer member 700, pinning means (not shown) may be applied to the implant 800 to ensure that the inner member 600 is not longitudinally disengaged from the outer member 700. The pinning means may include a clamp, a pin, a screw, or any other known mechanism suitable for retaining the inner member 600 to the outer member 700. Furthermore, the inclined side wall 706 of the outer member 700 prevents the inner member 600 from laterally disengaging from the outer member 700.

Figure 5:
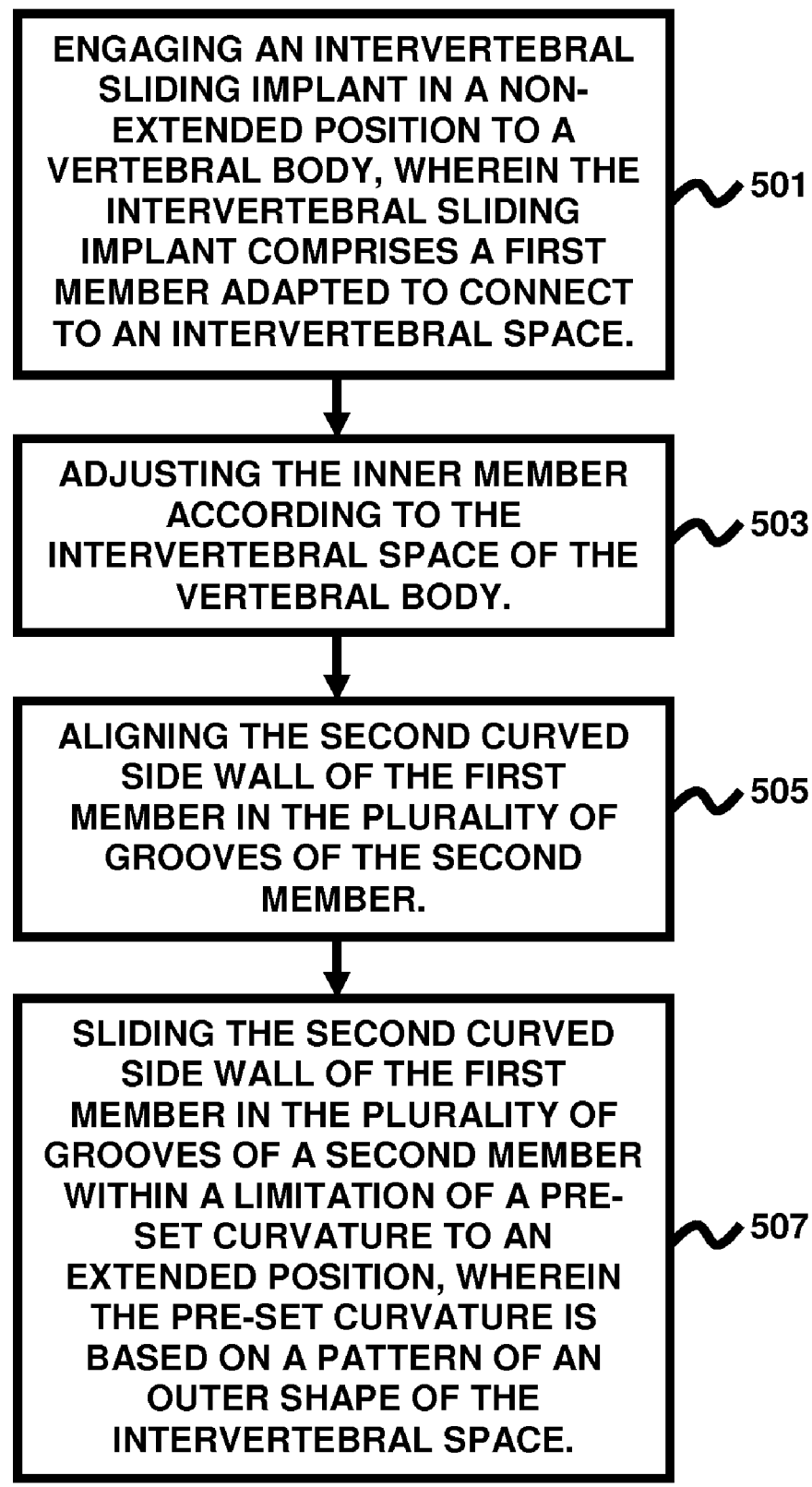
FIG. 5 is a process flow diagram illustrating a method of performing a surgical procedure according to an embodiment herein.

FIG. 5, with reference to FIGS. 1A through 4D, is a process flow that illustrates a method of performing a surgical procedure according to an embodiment herein, wherein the method comprises engaging (501) an intervertebral sliding implant in a non-extended position to a vertebral body, wherein the intervertebral sliding implant 800 comprises a first member 600 adapted to connect to an intervertebral space (not shown) between two adjacent vertebrae (not shown), wherein the first member 600 has a curved configuration and comprises a pair of curved side walls 610, 614 connected to each of a front wall 602, an upper curved wall 620, and a lower curved wall 618, wherein a length of a first curved side wall 610 is less than a length of each of a second curved side wall 614, the upper curved wall 620, and the lower curved wall 618, and wherein an edge of the second curved side wall 614 is offset from an edge of the front wall 602. The implant 800 further includes a second member 700 slidably attached to the first member 600, wherein the second member 700 has a curved configuration and comprises a top 702 and bottom 704 curved wall each connected to a truncated inclined side wall 706 and a guide wall 710 positioned opposite to the truncated inclined side wall 706, wherein the guide wall 710 comprises a plurality of oppositely positioned grooves 714, 716. The method further comprises adjusting (503) the inner member 600 according to the intervertebral space (not shown) of the vertebral body (not shown); aligning (505) the second curved side wall 614 of the first member 600 in the plurality of grooves 714, 716 of the second member 700; and sliding (507) the second curved side wall 614 of the first member 600 in the plurality of grooves 714, 716 of the second member 700 within a limitation of a pre-set curvature to an extended position, wherein the pre-set curvature is based on a pattern of an outer shape of the intervertebral space (not shown).

Preferably, the front wall 602 comprises a leg 605 positioned along an edge of the front wall 602 adjacent to the second curved side wall 614, and wherein a height of the leg 605 of the front wall 602 is substantially equal to a height of the first curved side wall 610. Furthermore, the height of each of the leg 605 of the front wall 602 and the first curved side wall 610 may be greater than a height of each of the front wall 602 and the second curved side wall 614. Additionally, the first member 600 and the second member 700 may be adapted to articulate from an extended position to a non-extended position as the first member 600 slides into the second member 700, and wherein the first curved side wall 610 of the first member 600 is adapted to connect to the truncated inclined side wall 706 of the second member 700 in the non-extended position. Preferably, each of the front wall 602, the first curved side wall 610, and the second curved side wall 614 of the first member 600 comprise a gap 604, 612, 616, respectively, wherein the method may further comprise inserting bone fusion material in the sliding intervertebral implant 800 through each the gap 604, 612, 616 in the non-extended position.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the appended claims.

What is claimed is:

1. A method of performing a surgical procedure, said method comprising:
  engaging an intervertebral sliding implant in a non-extended position to a vertebral body, wherein said intervertebral sliding implant comprises:
    a first member adapted to connect to an intervertebral space between two adjacent vertebrae, wherein said first member has a curved configuration and comprises a pair of curved side walls connected to each of a front wall, an upper curved wall, and a lower curved wall, wherein a length of a first curved side wall is less than a length of each of a second curved side wall, said upper curved wall, and said lower curved wall, and wherein an edge of said second curved side wall is offset from an edge of said front wall; and
    a second member slidably attached to said first member, wherein said second member has a curved configuration and comprises a top and bottom curved wall each connected to a truncated inclined side wall and a guide wall positioned opposite to said truncated inclined side wall, wherein said guide wall comprises a plurality of oppositely positioned grooves,
  adjusting said first member according to said intervertebral space of said vertebral body;
  aligning said second curved side wall of said first member in said plurality of grooves of said second member; and
  sliding said second curved side wall of said first member in said plurality of grooves of said second member within a limitation of a pre-set curvature to an extended position, wherein said pre-set curvature is based on a pattern of an outer shape of said intervertebral space, wherein said first member and said second member are adapted to articulate from said extended position to said non-extended position as said first member slides into said second member, and wherein said first curved side wall of said first member is adapted to connect to said truncated inclined side wall of said second member in said non-extended position.

2. The method of claim 1, wherein said front wall comprises a leg positioned along an edge of said front wall adjacent to said second curved side wall, and wherein a height of said leg of said front wall is substantially equal to a height of said first curved side wall.

3. The method of claim 2, wherein said height of each of said leg of said front wall and said first curved side wall is greater than a height of each of said front wall and said second curved side wall.

4. The method of claim 1, wherein each of said front wall, said first curved side wall, and said second curved side wall of said first member comprise a gap, wherein said method further comprises inserting bone fusion material in said sliding intervertebral implant through each said gap in said non-extended position.

5. A method comprising:
    positioning a first member into an intervertebral space between two adjacent vertebrae, wherein said first member comprises a substantially curved configuration and a pair of curved side walls operatively connected to each of a front wall, an upper curved wall, and a lower curved wall, wherein a length of a first curved side wall is less than a length of each of a second curved side wall, said upper curved wall, and said lower curved wall, wherein an edge of said second curved side wall is offset from an edge of said front wall, and wherein said front wall comprises a leg positioned along an edge of said front wall adjacent to said second curved side wall;
    positioning a second member to be operatively connected to said first member, wherein said second member comprises a substantially curved configuration and includes a top and bottom curved wall each operatively connected to a truncated inclined side wall and a guide wall, wherein said guide wall is positioned opposite to said truncated inclined side wall, wherein said guide wall comprises a plurality of oppositely positioned grooves, wherein said second curved side wall of said first member is adapted to slide in said plurality of oppositely positioned grooves of said guide wall of said second member within a limitation of a pre-set curvature, and wherein said pre-set curvature is based on a pattern of an outer shape of said intervertebral space;
    articulating said first member and said second member from an extended position to a non-extended position as said first member slides into said second member; and
    operatively connecting said first curved side wall of said first member to said truncated inclined side wall of said second member in said non-extended position.

6. The method of claim 5, wherein each of said first curved side wall and said second curved side wall of said first member comprises a gap.

7. The method of claim 5, wherein said front wall comprises a gap positioned offset from a center portion of said front wall.

8. The method of claim 7, further comprising inserting bone fusion material in said gap.

9. The method of claim 5, wherein a height of said leg of said front wall is substantially equal to a height of said first curved side wall.

10. The method of claim 9, wherein said height of each of said leg of said front wall and said first curved side wall is greater than a height of each of said front wall and said second curved side wall.

11. A method comprising:
    providing an inner member that is adapted to connect to an intervertebral space between two adjacent vertebrae, wherein said inner member comprises a front wall comprising a leg positioned on a lateral edge of said front wall; a first curved side wall connected to said front wall; a second curved side wall positioned opposite to said first curved side wall and behind said leg, wherein said second curved side wall is greater in length than said first curved side wall; an upper curved wall; and a lower curved wall positioned opposite to said upper curved wall;
    providing an outer member that is adapted to slidably attach to said inner member, wherein said outer member comprises a top curved wall matching an arcuate shape of said upper curved wall of said inner member; a bottom curved wall matching an arcuate shape of said lower curved wall of said inner member; a truncated inclined side wall connected to each of said top curved wall and said bottom curved wall; and a guide wall positioned opposite to said truncated inclined side wall and comprising a plurality of oppositely positioned grooves, said guide wall being connected to each of said top curved wall and said bottom curved wall;
    allowing said second curved side wall of said inner member to be adapted to slide in said plurality of oppositely positioned grooves of said guide wall of said outer member within a limitation of a pre-set curvature, wherein said pre-set curvature is based on a pattern of an outer shape of said intervertebral space;
    allowing said inner member and said outer member to be adapted to articulate from an extended position to a non-extended position as said inner member slides into said outer member; and
    allowing said first curved side wall of said inner member to be adapted to connect to said truncated inclined side wall of said outer member in said non-extended position.

12. The method of claim 11, wherein each of said first curved side wall and said second curved side wall of said inner member comprise a gap.

13. The method of claim 11, wherein said upper curved wall is greater in length than said first curved side wall.

14. The method of claim 11, wherein a height of said leg of said front wall is substantially equal to a height of said first curved side wall.

15. The method of claim 14, wherein said height of each of said leg of said front wall and said first curved side wall is greater than a height of each of said front wall and said second curved side wall.

16. The method of claim 11, wherein said front wall comprises a gap positioned offset from a center portion of said front wall.

17. The method of claim 16, further comprising configuring said gap to permit insertion of bone fusion material in said gap.

18. The method of claim 11, wherein said lower curved wall of said inner member is greater in length than said first curved side wall.

* * * * *